(12) United States Patent
Durand et al.

(10) Patent No.: US 6,841,171 B1
(45) Date of Patent: Jan. 11, 2005

(54) USE OF OYSTER FLESH ENZYMATIC HYDROLYSATES FOR PREPARING COMPOSITIONS ELIMINATING FREE RADICALS

(75) Inventors: Patrick Durand, Reze (FR); Annie Landrein, Nantes (FR); Philippe Roy, Nantes (FR); Albert Lindenbaum, Paris (FR); Marvin Edeas, Paris (FR)

(73) Assignees: Institut Francis de Recherche Pour l'Exploitation de la Recherche, Issy les Moulineaux (FR); Assistance Publique-Hopitaux de Paris, Paris (FR)

( * ) Notice: Subject to any disclaimer, the term of this patent is extended or adjusted under 35 U.S.C. 154(b) by 219 days.

(21) Appl. No.: 10/070,176
(22) PCT Filed: Sep. 1, 2000
(86) PCT No.: PCT/FR00/02420

§ 371 (c)(1),
(2), (4) Date: May 22, 2002

(87) PCT Pub. No.: WO01/17538

PCT Pub. Date: Mar. 15, 2001

(30) Foreign Application Priority Data

Sep. 3, 1999 (FR) ............................................. 99 11060

(51) Int. Cl.[7] ........................ A61K 35/56; A61K 38/01; A61K 7/48; A23L 1/29; C12P 21/06

(52) U.S. Cl. .............................. 424/547; 426/7; 426/55; 426/56; 426/63; 426/422; 426/424; 426/425; 426/332; 426/542; 435/68.1

(58) Field of Search .......................... 435/68.1; 426/547, 426/7, 422, 424, 425, 431, 55, 56, 63, 332, 542

(56) References Cited

U.S. PATENT DOCUMENTS

| | | | | |
|---|---|---|---|---|
| 5,834,048 A | * | 11/1998 | Erasmus et al. | 426/395 |
| 6,001,401 A | * | 12/1999 | Erasmus et al. | 426/118 |
| 6,007,860 A | * | 12/1999 | Erasmus et al. | 426/324 |
| 6,060,102 A | * | 5/2000 | Erasmus et al. | 426/395 |
| 6,165,539 A | * | 12/2000 | Erasmus et al. | 426/629 |

FOREIGN PATENT DOCUMENTS

| | | |
|---|---|---|
| JP | 48 022661 | 3/1973 |
| JP | 07 082132 | 3/1995 |
| JP | 07 102252 A | 4/1995 |
| JP | 10 236941 A | 9/1998 |
| NZ | 329 018 A | 4/2002 |

* cited by examiner

Primary Examiner—Herbert J. Lilling
(74) Attorney, Agent, or Firm—Alston & BIrd LLP

(57) ABSTRACT

The invention concerns the use of an oyster enzymatic hydrolysate for preparing a composition eliminating free radicals. The invention is characterized in that said hydrolysate is obtainable by hydrolysis of oyster flesh by a protease. The invention is applicable in therapy, dietetics and cosmetology.

6 Claims, 1 Drawing Sheet

Figure 1:
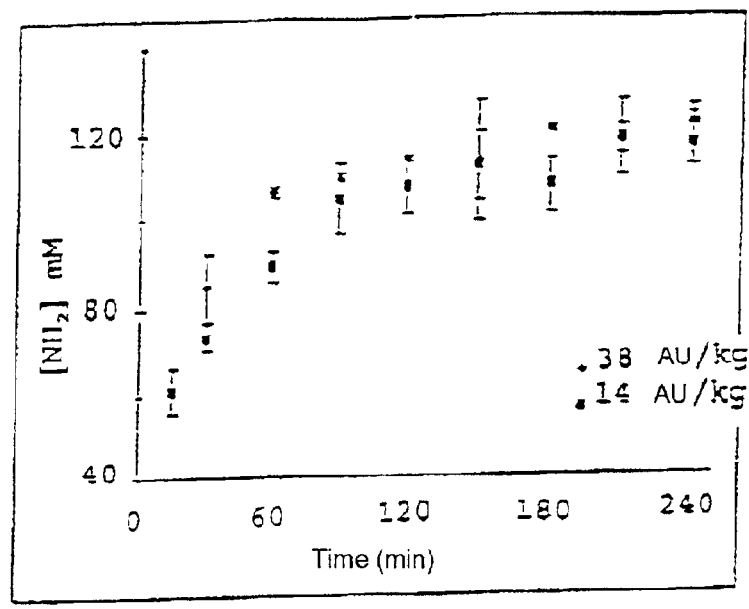

USE OF OYSTER FLESH ENZYMATIC HYDROLYSATES FOR PREPARING COMPOSITIONS ELIMINATING FREE RADICALS

The present invention relates to the use of enzymatic oyster flesh hydrolysates for preparing free-radical scavenging compositions, of use in particular in therapeutics, in dietetics and in cosmetology.

Oxygenated free radicals are atoms or molecules which have an unpaired electron in their outer orbital (OH—, $O_2^-$, ROO$^-$, RO$^-$, etc.). As a result, they are extremely unstable and can react with stable molecules such as lipids, carbohydrates, proteins or nucleic acids, which are fundamental elements of cells, so as to pair their electron, this reaction leading to a chain reaction of formation of new free radicals. Thus, they are capable of causing serious cellular modifications, such as mutation or cellular ageing, or even cell death.

At the cellular level, oxygenated free radicals are constantly being formed. They may also form during detoxification mechanisms after exposure to certain substances or under the effect of radiation. Normally, the endogenous production of oxygenated free radicals is counterbalanced by the presence of defense systems represented, firstly, by enzymes (superoxide dismutases, catalases, glutathione peroxidases) which intercept the active forms of the oxygen and, secondly, by "agents which trap free radicals" (glutathione, uric acid, vitamin C, vitamin A, vitamin E, taurine, etc.) which block membrane lipid peroxidation chain reactions, such that the organisms are not harmed by them.

However, many situations may lead to the excessive formation of oxygenated free radicals: intense exposure to sunlight, intoxication with certain chemical products and certain medicinal products, abrupt reoxygenation or hyperoxygenation of tissues previously deprived of oxygen, the occurrence of an intense (burns, infections, etc.) or chronic inflammatory reaction. An excess of oxygenated free radicals may also be linked to a genetic disease or to a decrease in defenses: immaturity of enzymatic systems in newborn babies, ageing, dietary deficiencies in vitamins and in trace elements (selenium, zinc, etc.).

Be that as it may, some responsibility in the genesis and maintenance of a certain number of chronic pathologies, such as atherosclerosis, malign ant conditions, inflammatory pathologies (Crohn's disease for example) and neurodegenerative pathologies (Alzheimer's disease, Parkinson's disease, etc.), or ageing, and also acute pathologies, such as post-ischemic reperfusion lesions, burns, septic shocks, viral infections, serious infectious conditions and allergies, have been attributed to an imbalance between the production and destruction of oxygenated free radicals, without it always being possible to specify whether these free radicals are the cause or the consequence, or both simultaneously, of the disease.

Consequently, it is understandable that a very large number of studies should currently be directed toward understanding more clearly the involvement of oxygenated free radicals in physiopathology, and toward developing compounds or compositions able to oppose the deleterious effects of these free radicals.

Some authors (Livingstone et al., 1990, Funct. Ecol. 4, 415–424; Regoli and Principato, 1995, Aquat. Tox., 31, 143–164) have demonstrated, in marine molluscs, not only the presence of superoxide dismutases, of catalases and of glutathione peroxidases, but also that of specific antioxidant enzymes such as glyoxalase, which catalyses the detoxification of ketoaldehydes formed during oxidative stress, and glutathione transferases, which catalyse a large variety of reactions conjugating glutathione to xenobiotic compounds, indicating that these organisms are capable of protecting themselves against oxygenated free radicals. Moreover, antioxidants, such as glutathione, vitamin A, vitamin E and taurine, have been detected in marine molluscs and have proved, in certain cases, to be quantitatively proportional to the oxidative stress experienced by these animals.

Thus, it has become apparent that marine molluscs may constitute a source of free-radical scavenging compounds which can be used in the prevention and treatment of the harmful effects of oxygenated free radicals.

A certain number of authors have more especially taken an interest in the free-radical scavenging potentials of oyster extracts. In particular:

Tapiero and Tew (Biomed. & Pharmacother., 1996, 50, 149–153) have studied the effects of an oyster lyophilisate, named JCOE (Japan Clinic Oyster Extract) on the intracellular content of glutathione-stimulating hormone (GSH), and also on the activity of glutathione-S-transferase (GST), of a culture of HL60 cells. This lyophilisate is obtained by heating oyster flesh at 80° C. for 1 hour then subjecting the resulting product to centrifugation and lyophilizing the supernatant thus collected. Tapiero and Tew thus demonstrated a significant increase in GSH synthesis in the HL60 cells cultured in the presence of the lyophilisate, without, however, noting any significant modification of the activity of GST.

Yoshikawa et al. (Biomed. & Pharmacother., 1997, 51, 328–332) have shown that an oyster lyophilisate, JCOE, is capable, in vitro, of trapping superoxide and hydroxyl radicals and of protecting rat gastric mucosa cells against the deleterious effects of hydrogen peroxide, when these cells are pretreated for 24 hours with this lyophilisate.

Kimura et al. (Journal of Ethnopharmacology, 1998, 59, 117–123) have shown that rats which are fed on peroxidized corn oil and receive, twice a day and orally, an aqueous oyster extract have serum levels of free fatty acids, triglycerides and lipid peroxides, and a hepatic level of total cholesterol, which are lower than those observed in rats fed in the same way but which do not receive aqueous oyster extract. Moreover, these authors have demonstrated the presence, in this aqueous extract, of a substance capable of both inhibiting adrenaline-induced lipolysis and stimulating lipogenesis from glucose in rat fat cells, which they have identified as being adenosine.

Nomura et al. have proposed, in the European Patent Application published under the no. 0 806 465 in the name of Japan Clinic Co. Ltd., preparing an antioxidant composition using a method consisting in fractionating with ethanol an aqueous oyster extract obtained beforehand by heating a mixture of oyster flesh and water at a temperature of between 50 and 90° C. for 2 to 3 hours. The antioxidant properties of the composition thus prepared are demonstrated, in that patent application, via tests aimed at assessing its ability to inhibit, in vitro, the reaction between superoxide anions produced by an enzymatic system xanthine—xanthine oxydase and 5,5-dimethyl-1-pyrrolen-1-oxide.

Dussart (Ifremer Report: Stage de VIème Année [6th Year training period], 1997, Faculté de Pharmacie, [School of Pharmacy], Université de Lille II [Lille II University]) has carried out a study aimed at comparing the free-radical scavenging properties of aqueous oyster extracts prepared by mixing material from ground oyster flesh with dionized water and then subjecting the resulting mixture to centrifugation followed by lyophilization of the supernatant, with those exhibited by oyster extracts prepared by subjecting material from grinding oysters to lyophilization only. The results of this study show that, while both types of oyster extract have, in vitro, a protective effect against oxidations induced, firstly, by a generator of peroxide radicals on hematocytes and, secondly, by copper on low density lipoproteins (LDLs), the aqueous oyster extracts appear to exhibit the most advantageous antioxidant potential.

It has, moreover, been proposed, in the Japanese Patent Applications published under no. 7-082132 and no. 7-102252, to use, in cosmetic compositions, hydrolysates prepared from oyster mucus, as antioxidant agents able to prevent skin ageing and in particular the appearance of wrinkles. These hydrolysates are obtained by centrifuging or pressing oysters, after extraction from their shells, and removing the flesh.

The mucus is then subjected to a series of fractionations with ethanol to rid it of the sodium chloride which it contains, and then to proteolysis. In Japanese Patent Application No. 7-102252, the mucus, once hydrolyzed, is subjected to a further desalifying operation, again using ethanol, in order to decrease its coloration.

The cost of manufacturing such hydrolysates is very high, in particular because of the not insignificant amounts of ethanol used during the desalifying operations and the need to have specific and relatively expensive installations due to the use of organic solvents. Because of this, regardless of knowing whether they exhibit significant free-radical scavenging activity, it is not desirable to use this type of hydrolysate for manufacturing free-radical scavenging compositions on an industrial scale, in particular if these compositions are intended to be marketed as food supplements.

Now, in the context of their studies, the inventors have noted that oyster hydrolysates obtained by subjecting oyster flesh to the action of a protease under suitable conditions exhibit, surprisingly, a free-radical scavenging activity which is even higher than that observed for the aqueous oyster extracts tested by Dussart in the abovementioned study, and may therefore advantageously be used for manufacturing compositions intended to prevent or treat the deleterious effects of oxygenated free radicals.

A subject of the present invention is therefore the use of an enzymatic oyster hydrolysate for preparing a free-radical scavenging composition, this use being characterized in that said hydrolysate can be obtained by hydrolyzing oyster flesh using a protease.

According to a first advantageous arrangement of the invention, the hydrolysis of the oyster flesh is carried out using a protease chosen from subtilisin, pepsin and trypsin. In fact, besides the fact that the cost of these proteases is compatible with industrial exploitation of the invention, they have the advantage of being part of the enzymes whose use is authorized in a large number of countries for preparing protein hydrolysates used in manufacturing food supplements.

Since proteases are not all active within the same pH and temperature ranges, the pH and temperature conditions under which the hydrolysis of the oyster flesh is performed depend on the protease chosen to carry out this hydrolysis.

Preferably, these pH and temperature conditions are such that they make it possible to obtain optimum activity of the protease. Thus, for example, the hydrolysis is preferentially carried out at a pH of approximately 8 and a temperature of approximately 60° C. in the case of subtilisin, at a pH of approximately 2 and a temperature of approximately 40° C. in the case of pepsin, and at a pH of approximately 8 and a temperature of approximately 37° C. in the case of trypsin.

According to another advantageous arrangement of the invention, the hydrolysis of the oyster flesh is carried out for a period of time sufficient for the hydrolysate to exhibit a degree of protein hydrolysis at least equal to 30%, and preferably to 50%, this degree of protein hydrolysis being determined by the equation below (Adler-Nissen, 1977, Proc. Biochem., 12, 18–23):

$$DH = (h/h \text{ total}) \times 100$$

in which:

h total represents the total number of peptide bonds present in the oyster flesh at the start of hydrolysis, whereas h represents the number of peptide bonds hydrolyzed during the hydrolysis, and is determined by the difference between the number of free amino (or carboxylic) ends present in the hydrolysate at the end of the hydrolysis ($h_1$) and the number of free amino (or carboxylic) ends present in the ground material at the start of the hydrolysis ($h_0$).

For the purposes of the present invention, the start of the hydrolysis corresponds to the moment at which the protease is brought into contact with the oyster flesh, while its end corresponds to the moment at which the hydrolysis is stopped by inactivation of said protease, for example by heat denaturation or by modification of the pH.

The total number of peptide bonds (h total) present in the oyster flesh can be obtained by the difference between the amount of total amino acids (free+bound) and the amount of free amino acids which this flesh contains. These amounts of total and free amino acids may be determined, for example, using a kit such as that marketed under the trademark Waters AccQ-Tag Chemistry Package® by the company Waters. The number of peptide bonds hydrolyzed (h) during the hydrolysis is, itself, obtained by the difference between the amount of free amino ends ($h_1$) present in the hydrolysate at the end of the hydrolysis and the amount of free amino ends ($h_0$) present in the oyster flesh at the start of the hydrolysis, which can be determined, for example, by reaction with fluorodinitrobenzene according to the protocol described in Biochem. J., 45, 563, 1949.

Here also, the amount of time for which the hydrolysis should be allowed to proceed in order to obtain a hydrolysate having a degree of protein hydrolysis at least equal to 30%, and preferably to 50%, depends on the protease chosen to carry out this hydrolysis and, for the same protease, on the pH and temperature conditions under which the hydrolysis is carried out and also on the dose at which this protease is used, the hydrolysis in fact occurring more rapidly, the higher the dose of protease.

According to another advantageous arrangement of the invention, the hydrolysate may be obtained using a method comprising, prior to the hydrolysis, an operation consisting in draining the oyster flesh. In accordance with the invention, this operation may be carried out by simply leaving the oysters, once extracted from their shells, to stand in a drainer, preferably at a temperature of between 4 and 8° C. so as to prevent any modification of the flesh, this being until no more liquid flows into said drainer.

According to a preferred arrangement of the invention, the hydrolysate may be obtained using a method comprising, prior to the hydrolysis, an operation consisting in grinding the oyster flesh, optionally followed by an operation consisting in diluting the resulting ground material in water.

Particularly preferably, the grinding operation is carried out after an operation consisting in draining the oyster flesh.

According to yet another advantageous arrangement of the invention, the hydrolysis is stopped by heat denaturation of the protease.

According to yet another advantageous arrangement of the invention, the hydrolysate may be obtained using a method which also comprises an operation consisting in collecting the liquid phase of the hydrolysate as it is at the end of the hydrolysis. This collection, which is intended to eliminate the various debris (shell debris, membrane debris, etc.) which may be present in this hydrolysate, may be carried out using any techniques conventionally used to separate a liquid phase from a solid phase, such as centrifugation, ultra-centrifugation, filtration or microfiltration, these techniques possibly being advantageously combined with one another.

According to another preferred arrangement of the invention, the hydrolysate may be obtained using a method which comprises the following steps:

a) grinding predrained oyster flesh,
b) diluting the ground material in water, at a ground material/water ratio of between 30/70 and 70/30 (m/v), and preferably between 40/60 and 60/40 (m/v),
c) hydrolyzing the ground material thus diluted with subtilisin at a pH of approximately 8 and at a temperature of approximately 60° C. for a period of time sufficient for the hydrolysate to exhibit a degree of protein hydrolysis at least equal to 50%,
d) stopping the hydrolysis by inactivation of the subtilisin, and
e) collecting the liquid phase of the hydrolysate.

According to yet another preferred arrangement of the invention, the hydrolysate may be obtained using a method which comprises the following steps:

a) grinding predrained oyster flesh,
b) diluting the ground material in water, at a ground material/water ratio of between 30/70 and 70/30 (m/v), and preferably between 40/60 and 60/40 (m/v),
c) hydrolyzing the ground material thus diluted with pepsin, at a pH of approximately 2 and at a temperature of approximately 400° C., for a period of time sufficient for the hydrolysate to exhibit a degree of protein hydrolysis at least equal to 50%,
d) stopping the hydrolysis by inactivation of the pepsin, and
e) collecting the liquid phase of the hydrolysate.

According to yet another preferred arrangement of the invention, the hydrolysate may be obtained using a method which comprises the following steps:

a) grinding predrained oyster flesh,
b) diluting the ground material in water, at a ground material/water ratio of between 30/70 and 70/30 (m/w), and preferably between 40/60 and 60/40 (m/v),
c) hydrolyzing the ground material thus diluted with trypsin, at a pH of approximately 8 and at a temperature of approximately 37° C., for a period of time sufficient for the hydrolysate to exhibit a degree of protein hydrolysis at least equal to 50%,
d) stopping the hydrolysis by inactivation of the trypsin, and
e) collecting the liquid phase of the hydrolysate.

Such enzymatic oyster hydrolysates have free-radical scavenging properties which, besides being pronounced, are extremely advantageous since they prove to be capable not only of neutralizing the effects of oxygenated free radicals produced during peroxidation reactions, but also of preventing the formation of these free radicals, through what appears to be a mechanism of chelation of the metals, such as for example copper, which are involved in the genesis of said free radicals.

In addition, they have the advantage of being possible to obtain using a method which is simple to carry out and economically compatible with industrial demands, in particular due to the fact that it requires the use of no organic solvent.

These hydrolysates are therefore capable of advantageously being used for preparing:

pharmaceutical compositions intended to treat pathologies which appear to be linked to an imbalance between the production and the destruction of oxygenated free radicals, as mentioned above, food supplements suitable for use either as adjuvants to a medical treatment or in a preventive capacity, in particular by individuals in whom it is desirable to reinforce the natural mechanisms of defense against oxygenated free radicals, because these defense means are physiologically decreased (elderly individuals, individuals suffering from dietary deficiencies in vitamins and trace elements, etc.) or because these individuals are led to find themselves in situations which promote the excessive formation of oxygenated free radicals (intense exposure to sunlight, exposure to chemical products, etc.), or cosmetic compositions aimed at preventing or treating skin ageing, the cause of which is largely inked to the free radicals generated in the skin by ultraviolet radiation.

To this end, they may be used either as they are, i.e. in aqueous form or, optionally, in the form of dry powders obtained, for example, by lyophilization, or mixed with physiologically acceptable excipients and/or other active substances, and in particular substances also having intrinsic free-radical scavenging properties and capable of acting synergistically (vitamins A, C or E, for example), within more complex formulations.

Figure 2:
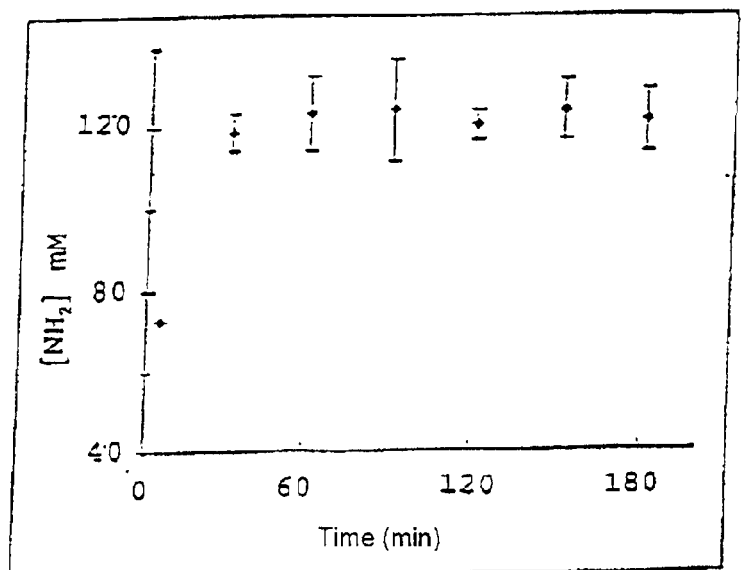

Besides the arrangements above, the invention also comprises other arrangements which will emerge from the further description which follows, which refers to examples illustrating the hydrolytic activity of enzymes on ground materials from oyster flesh, the preparation of enzymatic oyster flesh hydrolysates and also the biological properties of these hydrolysates, and which refers to the attached drawings in which:

FIG. 1 represents the kinetics of two hydrolyses carried out on ground materials from oyster flesh, with two different doses of subtilisin; while FIG. 2 represents the kinetics of a hydrolysis carried out on ground material from oyster flesh with pepsin.

It goes without saying, however, that these examples are given only by way of illustration of the subject of the invention, and in no way constitute a limitation thereof.

EXAMPLE 1

Study of the Hydrolytic Activity of Subtilisin on Ground Materials from Oyster Flesh Live *Crassostrea gigas* hollow oysters, originating from the Ifremer experimental shellfish breeding station at Bouin (Vendée—France), after extraction from their shells, are drained on a metal sieve for 1 hour at a temperature of between 4 and 8° C., and then ground for 2 minutes at 1000 rpm using an Ultra-Turrax® (maximum power equal to 170 W at 2000 rpm).

The ground material obtained, after optional storage at a temperature of −20° C. and, in that case, thawing, is introduced into a reactor. 60% (v/m) of deionized water are added, with stirring. A dose of 14 AU (active units) or of 38 AU of subtilisin (marketed under the trademark alcalase® 2.4 L by the company Novo Nordisk) per kg of the mixture which the reactor contains are then introduced into it, still with stirring. The temperature of the reactor is maintained at 60° C. throughout the hydrolysis, i.e. for 4 hours. The stirring is also maintained and the pH is regulated using a pH-stat so as to be constantly at a value of 8.

After 4 hours of hydrolysis, the subtilisin activity is stopped by heat denaturation of the latter, by placing the reaction mixture in a wash bath at 90° C. for 25 minutes.

Samples are taken from the reactor, by means of a peristaltic pump, just before the subtilisin is introduced therein ($t_0$), then 15 and 30 minutes after the introduction of this enzyme into the reactor (i.e. at $t_{15}$ and $t_{30}$), and then every 30 minutes, this being until the hydrolysis is stopped (i.e. at $t_{60}$, $t_{90}$, $t_{120}$, $t_{150}$, $t_{180}$, $t_{210}$ and $t_{240}$). The samples which contain the subtilisin are placed in a water bath at 90° C. for 25 minutes so as to stop the activity of the latter. All the samples are then subjected to centrifugation at 13,000 rpm. The supernatants are filtered through a 0.7 µm membrane, and then through a 0.16 µm membrane.

The hydrolytic activity of the subtilisin is assessed by monitoring:

firstly, the evolution of the concentration in the ground materials of free amino ends between $t_{15}$ and $t_{240}$, by assaying these ends by reaction with fluorodinitrobenzene, this monitoring making it possible to establish the kinetics of the hydrolysis, and secondly, the evolution of the degree of protein hydrolysis (DH) of the ground materials between $t_{15}$ and $t_{240}$, this degree of protein hydrolysis being calculated according to the equation (DH=(h/h total)×100, in which h total is obtained by assaying the total and free amino acids present in the ground materials using a Waters AccQ-Tag Chemistry Package® kit, while h is determined by assaying the free amino ends present in the samples taken at $t_{15}$, $t_{30}$, etc., up to $t_{240}$ inclusive, by reaction with fluorodinitrobenzene.

FIG. 1 represents the kinetics of the hydrolysis carried out with the 14 AU/kg (■) dose of subtilisin and that carried out with the 38 AU/kg (♦) dose of subtilisin, the values of the concentrations of free amino ends being expressed in mM along the y-axis and the time being expressed in minutes along the x-axis.

This figure shows that the hydrolysis is more rapid when the subtilisin dose is increased. Thus, the plateau is reached after 90 minutes of hydrolysis for the 14 AU/kg dose, and this period of time is reduced to 60 minutes for 38 AU/kg dose. However, the concentration of free amino ends for which the plateau is reached is similar for both doses of enzyme. The same is true for the final concentration of free amino ends (approximately 120 mM).

Table I below shows the values of the degrees of protein hydrolysis (DH), expressed as percentages, obtained for each of the subtilisin doses.

TABLE I

| Time | DH (%) | |
|---|---|---|
| (minutes) | 14 AU/kg | 38 AU/kg |
| 15 | 14 | — |
| 30 | 23 | 31 |
| 60 | 34 | 46 |
| 90 | 45 | 48 |
| 120 | 47 | 51 |
| 150 | 50 | 51 |
| 180 | 47 | 56 |
| 210 | 54 | 54 |
| 240 | 54 | 58 |

This table shows that, whatever the subtilisin dose used, the rate of hydrolysis decreases when 45% of the potentially hydrolyzable peptide bonds have been broken. The hydrolysis continues, however, but lightly, since the final values of the degree of protein hydrolysis exceed 50%, to reach 54% in one case and 58% in the other case.

EXAMPLE 2

Study of the Hydrolytic Activity of Pepsin on Ground Materials from Oyster Flesh The hydrolytic activity of pepsin on ground materials from oyster flesh is assessed using a procedure identical to that used in example 1, with the exception that the hydrolysis is carried out with a dose of 1% by mass of pepsin relative to the total mass of the ground material/deionized water mixture present in the reactor, at a temperature of 40° C. and at a pH equal to 2.

FIG. 2 represents the kinetics of the hydrolysis thus obtained, the values of the concentrations of free amine functions being expressed in mM along the y-axis, the time being expressed in minutes along the x-axis.

This figure shows that the hydrolysis clearly takes place more rapidly than when it is carried out with subtilisin, even at the dose of 38 AU/kg, since the plateau is reached 30 minutes after introducing the pepsin into the reactor. However, the final concentration of free amine functions in the hydrolysate, which is around 120 mM, is entirely comparable to that obtained when hydrolysis is carried out with subtilisin.

EXAMPLE 3

Preparation of Enzymatic Oyster Flesh Hydrolysates Using Subtilisin

On the basis of the results obtained in the study which is the subject of example 1, two hydrolysates which exhibit different degrees of protein hydrolysis are prepared—which will hereinafter be named, respectively, hydrolysate A and hydrolysate B—by subjecting two ground materials from predrained oyster flesh to hydrolysis with subtilisin.

The ground materials from oyster flesh are prepared and the hydrolyses are carried out under the same conditions as those described in example 1, using a subtilisin dose of 38 AU per kg of ground material/deionized water mixture.

For hydrolysate A, the hydrolysis is stopped 4 hours after introduction of the enzyme into the reactor, so that it exhibits a maximum degree of protein hydrolysis, i.e. close to 60%.

For hydrolysate B, the hydrolysis is stopped 30 minutes after introduction of the enzyme into the reactor, so that it exhibits a degree of protein hydrolysis substantially equal to half the maximum degree of protein hydrolysis, i.e. approximately 30%.

In both cases, the hydrolytic activity of the subtilisin is stopped by placing the reaction mixtures in a water bath at 90° C. for 25 minutes. The mixtures are then centrifuged at 4000 rpm. The supernatants are filtered through a 0.7 μm membrane and then through a 0.16 μm membrane. The hydrolysates thus prepared have a granular appearance browny-green in color. They are lyophilized and placed in flasks at −20° C.

EXAMPLE 4

Biochemical characterization of an Enzymatic Oyster Flesh Hydrolysate Obtained in Accordance with the Invention A study is carried out aimed at determining, for hydrolysate A prepared according to example 3:
 its solids content,
 its content of inorganic material,
 its content of soluble proteins,
 its content of total sugars and of glycogen, and also
 its content and its composition of total amino acids and of free amino acids,
and at comparing the results with those obtained under the same conditions, firstly, for ground material from oyster flesh prepared as described in example 1 and, secondly, for an aqueous oyster extract prepared:
 by mixing ground material from oyster flesh with deionized water (1/3, v/v) until a homogeneous mixture is obtained, then
 subjecting the resulting mixture to centrifugation at 3000 g for 20 minutes, and
 lyophilizing the supernatant collected at the end of this centrifugation.

The solids content is determined by placing samples of hydrolysate A at a temperature of 100° C. until a constant weight is obtained (6 hours minimum) and calculating the percentage represented by this weight relative to the initial weight of these samples.

The content of inorganic material is determined by incinerating samples of hydrolysate A at a temperature of 600° C. for 12 hours and calculating the percentage represented by the weight of the residue relative to the weight of the solids.

The soluble proteins are assayed using the kit marketed by the company Pierce under the commercial name BCA® Protein Assay Reagent. Bovine albumin is used as a standard.

The total sugars and the glycogen are assayed according to the method described by M. Dubois et al., (Anal. Chem., 1956, 28, 350–356). For these assays, the samples are delipidized beforehand according to the method of E. G. Blight and W. J. Dyer (Can. J. Biochem. Physiol., 1959, 37, 911–917).

The content and the composition of total amino acids and of free amino acids are, themselves, determined using a Waters AccQ-Tag Chemistry Package® kit. For assaying the total amino acids, the samples of hydrolysate A are subjected, beforehand, to acid hydrolysis via the action of 6N HCl for 12 hours at 110° C. under vacuum, whereas, for assaying the free amino acids, sulfosalicylic acid is added, beforehand, to the samples of hydrolysate A and the mixture is centrifuged in order to cause the proteins present in the samples to precipitate.

Table II below shows the solids content and the contents of inorganic material, of soluble proteins, of total sugars, of glycogen, of total amino acids and of free amino acids exhibited, respectively, by hydrolysate A, the ground material from oysters and the aqueous oyster extract.

The solids contents are expressed as percentages relative to the lyophilized weight (% w/w) of the samples, except in the case of the ground material, for which the solids are expressed as percentage relative to the fresh weight (I w/w*) of the samples. The contents of inorganic material, of soluble proteins, of total sugars, of glycogen, of total amino acids and of free amino acids are expressed as percentages relative to the dry weights (% w/w) of the samples.

TABLE II

|  | Hydrolysate A | Ground material | Aqueous extract |
|---|---|---|---|
| Solids | 96.23 (% w/w) | 10.20 (% w/w*) | 95 (% w/w) |
| Inorganic material (% w/w) | 36.43 | 37.33 | 37 |
| Soluble proteins (% w/w) | 13.25 | 30 | 15 |
| Total sugars (% w/w) | 8.52 | 6.63 | 3.7 |
| Glycogen (% w/w) | 1.29 | 1 | 1.5 |
| Total amino acids (% w/w) | 35.1 | 36.7 | 20.15 |
| Free amino acids (% w/w) | 17.8 | 7 | 8.10 |

Table III below itself shows the compositions of total and free amino acids of hydrolysate A, of the ground material from oysters and of the aqueous oyster extract. The contents of each amino acid are expressed as percentages relative to the total weight (% w/w) of the amino acids present in the samples.

TABLE III

|  | HYDROLYSATE A | | GROUND MATERIAL | | AQUEOUS EXTRACT | |
|---|---|---|---|---|---|---|
| Amino acids | Total AA (% w/w) | Free AA (% w/w) | Total AA (% w/w) | Free AA (% w/w) | Total AA (% w/w) | Free AA (% w/w) |
| Taurine | 10.67 | 19.25 | 11.48 | 55.98 | 30.47 | 60.66 |
| Hydroxyproline | — | — | — | — | — | — |
| Aspartic acid | 10.08 | 2.45 | 10.43 | 4.79 | 11.26 | 0.72 |
| Threonine | 5.02 | 4.07 | 4.79 | — | 4.16 | — |
| Serine | 4.67 | 6.58 | 5.02 | 2.28 | 4.46 | 2.21 |
| Glutamic acid | 13.26 | 8.08 | 13.49 | 8.60 | 11.91 | 11.46 |
| Proline | 5.12 | 2.20 | 4.85 | 7.59 | — | — |
| Glycine | 6.31 | 3.61 | 6.49 | 6.81 | 5.31 | 5.05 |

TABLE III-continued

| Amino acids | HYDROLYSATE A | | GROUND MATERIAL | | AQUEOUS EXTRACT | |
|---|---|---|---|---|---|---|
| | Total AA (% w/w) | Free AA (% w/w) | Total AA (% w/w) | Free AA (% w/w) | Total AA (% w/w) | Free AA (% w/w) |
| Alanine | 5.64 | 6.43 | 4.39 | 3.21 | 5.80 | 8.01 |
| Cysteine | — | — | — | — | — | — |
| Valine | 4.51 | 4.94 | 4.16 | 0.42 | 2.77 | — |
| Methionine | 2.13 | 2.76 | 2.06 | — | 1.53 | — |
| Isoleucine | 4.02 | 4.38 | 3.36 | — | 2.58 | — |
| Leucine | 6.18 | 7.63 | 6.32 | 0.65 | 4.66 | — |
| Tyrosine | 3.39 | 5.04 | 3.27 | — | 1.73 | 2.95 |
| Phenylalanine | 3.53 | 4.71 | 3.29 | 0.26 | 2.72 | — |
| Hydroxylysine | — | — | — | — | — | — |
| Lysine | 6.28 | 7.00 | 7.04 | 3.59 | 5.21 | 0.73 |
| Histidine | 2.33 | 2.92 | 2.92 | 1.70 | 1.24 | — |
| Arginine | 6.86 | 7.94 | 6.65 | 4.11 | 4.16 | 1.72 |

Table II shows that hydrolysate A has a content of total sugars greater than that found in the ground material and in the aqueous extract. This increase is due to the destructuring of tissues caused by the enzymatic hydrolysis, thus allowing greater solubilization of the sugars. The decrease in the content of soluble proteins which is observed between the ground material and the hydrolysate is a consequence of the hydrolysis of the native proteins. This hydrolysis generates a considerable amount of free amino acids and peptides which are relatively unreactive with the reagent used to assay the soluble proteins (BCA®). On the other hand, the content of inorganic materials does not vary between the three preparations.

Moreover, it results from Table II that the content of free amino acids in hydrolysate A is notably higher than the content of free amino acids in the aqueous oyster extract, the latter being very close to that found for the ground material from oyster flesh. The increase in the amount of free amino acids present in hydrolysate A is directly linked to the breaking of peptide bonds caused by the hydrolysis reaction.

However, in view of Table III, it appears that the proportion of free taurine, which is known to have antioxidant activity, is lower in hydrolysate A than in the aqueous oyster extract. Specifically, taurine in free form represents 60.66% of the free amino acids in the aqueous oyster extract against only 19.25% in hydrolysate A.

EXAMPLE 5

Biological Activity of the Enzymatic Oyster Flesh Hydrolysates Obtained in Accordance with the Invention The biological activity of hydrolysates A and B prepared according to example 3 is assessed via a series of experiments aimed at testing:
  firstly, the ability of these hydrolysates to inhibit hemolysis induced by introducing a peroxide radical generator, namely 2,2'-azobis(2-amidinopropane) dihydrochloride (AAPH), into a suspension of hematocytes, and
  secondly, the ability of these hydrolysates to protect low density lipoproteins (LDLs) against copper-induced oxidation.

5.1—Inhibition of AAPH-Induced Hemolysis:
a) Protocol 5 ml of human blood are taken into an EDTA tube (which is immediately placed in crushed ice) and centrifuged for 10 minutes at 1000 g and at 4° C. The plasma is removed and the hematocytes are washed 3 times with a 9% NaCl solution with PBS buffer (pH 7.4). 200 µl of the hematocyte cell pellet are then diluted in 9.8 µl of 9% NaCl solution or of PBS buffer.

Firstly, the cell suspension obtained is brought into contact, for 10 minutes, with the solutions (9% NaCl or PBS) of hydrolysate A or B, the volume of which is calculated such that the final solution corresponds to 25, 50 and 100 mg/l. A sample: without hydrolysate constitutes the control.

300 µl of a solution of AAPH preincubated at 37° C. are then introduced into the hematocyte suspensions and the entire mixture is placed, with gentle stirring, in a water bath for 40 minutes.

In parallel, a sample of the hematocyte suspension (without AAPH or product) is placed at −80° C. for 1 hour.

The hematocyte lysis is assessed by measuring lactate dehydrogenase (LDH) activity using a Hitachi® 911 automatic machine. Each measurement is taken in duplicate.

The LDH activity determined on the samples placed at −80° C. corresponds to the total hematocyte hemolysis.

The LDH activity determined on the samples which did not contain hydrolysate corresponds to the sensitivity of the hematocytes to the "free-radical stress" under the experimental conditions. This measurement makes it possible, moreover, to verify that the experimental conditions (hemolysis <100%) are suitable for the study.

For each concentration of hydrolysate, the LDH activity is compared to the activity of the samples which do not contain any product, and expressed as percentage activity.
b) Results:

Table IV below shows the mean of the percentages of inhibition (Ia) obtained for solutions of 25, 50 and 100 mg/l of hydrolysate A and of hydrolysate B.

TABLE IV

| Concentration | Ia (%) | |
|---|---|---|
| (mg/l) | Hydrolysate A | Hydrolysate B |
| 25 | 38 | 25 |
| 50 | 74 | 48 |
| 100 | 96 | 98 |

This table shows that the enzymatic oyster flesh hydrolysates obtained in accordance with the invention exhibit a marked ability to inhibit the hemolysis induced by introducing a peroxide radical generator into a suspension of hematocytes, which means that they are capable of neutralizing the oxidant effects of these peroxide radicals, since the inhibitory concentration 50 (IC$_{50}$) of hydrolysate A is between 25 and 50 mg/l, whereas that of hydrolysate B comes to 50 mg/l.

By way of comparison, the inhibitory concentration 50 (IC$_{50}$) obtained by Dussart (ibid) for an aqueous oyster extract is 275 mg/l.

5.2 Protection of LDLs Against Copper-Induced Oxidation:

a) Protocol;

The LDLs are prepared from 100 ml of plasma (blood taken on EDTA). Firstly, the VLDLs are removed by ultracentrifugation for 24 hours at 40,000 g (density; 1.019). A second ultracentrifugation, for 24 hours at 40,000 g (density: 1.063), enables the LDLs to be obtained. The LDLs are then dialyzed for 24 hours at 4° C. against Tris-EDTA buffer, aliquoted and then stored at 4° C.

The LDLs (0.2 mg of protein/ml of solution), dialyzed beforehand against PBS buffer, are incubated for 24 hours at 37° C. in the presence of copper (oxidant) and in the presence or absence of the products studied.

For each study, 3 determinations are therefore made in parallel:

LDL in the absence of copper (native LDL control),

LDL in the presence of 5 µM of copper sulfate (oxidized LDL control),

LDL in the presence of 5 µM of copper sulfate and of increasing concentrations of hydrolysates A and B.

After the oxidation has been stopped with BHT/EDTA, the LDL solution is dialyzed for 24 hours at +4° C. and filtered through a 0.2 µm "millipore" membrane.

The inhibitory effect of the hydrolysates with respect to the LDL oxidation by the copper is quantified by assaying 2 lipoperoxidation markers:

MDA (malondialdehyde), for calculating the percentage of inhibition Ib, hydroperoxides, for calculating the percentage of inhibition Ic.

MDA Assay

MDA forms, with thiobarbituric acid, when hot and in acid medium, a fluorescent chromogenic complex. After extraction with normal butanol, the intensity of the fluorescence is measured using a spectrofluorometer. The MDA concentrations are determined by means of an MDA range extending from 0.2 to 1 nmol.

Hydroperoxide Assay

Hydroperoxides release iodine from a stabilized solution of potassium iodide. The released iodine is measured by determining the optical density (OD) at 365 nm.

The iodine concentration of the sample is then calculated from the extinction coefficient $\epsilon$ (=2.46 104, 1 cm, 1M) of this element.

b) Results:

Tables V and VI below show, respectively, the percentages of inhibition (Ib) and (Ic) as obtained for solutions of 25, 50, 100 and 250 mg/l of hydrolysate A and of hydrolysate B.

TABLE V

| Concentration | Ib (%) | |
|---|---|---|
| (mg/l) | Hydrolysate A | Hydrolysate B |
| 25 | −9 | 40 |
| 50 | 75 | 82 |
| 100 | 73 | 86 |
| 250 | 86 | 89 |

TABLE VI

| Concentration | Ic (%) | |
|---|---|---|
| (mg/l) | Hydrolysate A | Hydrolysate B |
| 25 | 10 | 71 |
| 50 | 100 | 100 |
| 100 | 100 | 100 |
| 250 | 100 | 100 |

These tables show that the enzymatic oyster flesh hydrolysates obtained in accordance with the invention also have a pronounced ability to oppose copper-induced LDL oxidation, this being an ability which may be linked to a chelating effect with respect to metals.

What is claimed is:

1. A method of preparing a free-radical scavenging composition, comprising hydrolyzing oyster flesh using a protease to obtain an enzymatic oyster hydrolysate, wherein the hydrolysate is obtained using a method comprising the following steps:

a) grinding predrained oyster flesh, b) diluting the ground material in water, at a ground material/water ratio of between 30/70 and 70/30 (m/v), c) hydrolyzing the ground material thus diluted with subtilisin at a pH of approximately, 8 and at a temperature of approximately 60° C. for a period of time sufficient for the hydrolysate to exhibit a degree of protein hydrolysis at least equal to 50%, d) stopping the hydrolysis by inactivation of the subtilisin, and e) collecting the liquid phase of the hydrolysate.

2. A method of preparing a fee-radical scavenging composition, comprising hydrolyzing oyster flesh using a protease to obtain an enzymatic oyster hydrolysate, wherein the hydrolysate is obtained using a method comprising the following steps:

a) grinding predrained oyster flesh, b) diluting the ground material in water, at a ground material/water ratio of between 30/70 and 70/30 (m/v), c) hydrolyzing the ground material thus diluted with pepsin, at a pH of approximately 2 and at a temperature of approximately 40° C. for a period of time sufficient for the hydrolysate to exhibit a degree of protein hydrolysis at least equal to 50%, d) stopping the hydrolysis by inactivation of the pepsin, and e) collecting the liquid phase of the hydrolysate.

3. A method of preparing a free-radical scavenging composition, comprising hydrolyzing oyster flesh using a protease to obtain enzymatic oyster hydrolysate, wherein the hydrolysate is obtained using a method comprising the following steps:

a) grinding predrained oyster flesh, b) diluting the ground material in water, at a ground material/water ratio of between 30/70 and 70/30 (m/w), c) hydrolyzing the ground material thus diluted with trypsin, at a pH of approximately 8 and at a temperature of approximately 37° C., for a period of time sufficient for the hydrolysate to exhibit a degree of protein hydrolysis at least equal to 50%, d) stopping the hydrolysis by inactivation of the trypsin, and e) collecting the liquid phase of the hydrolysate.

4. A food supplement comprising a free-radical scavenging composition obtained by the method of claim 1.

5. A food supplement comprising a free-radical scavenging composition obtained by the method of claim 2.

6. A food supplement comprising a free-radical scavenging composition obtained by the method of claim 3.

* * * * *

UNITED STATES PATENT AND TRADEMARK OFFICE
CERTIFICATE OF CORRECTION

PATENT NO. : 6,841,171 B1
DATED : January 11, 2005
INVENTOR(S) : Durand et al.

It is certified that error appears in the above-identified patent and that said Letters Patent is hereby corrected as shown below:

<u>Title page,</u>
Item [73], Assignee, "Francis" should read -- Francais --.

Signed and Sealed this

Fifth Day of April, 2005

JON W. DUDAS
*Director of the United States Patent and Trademark Office*